(12) United States Patent
Venkatesh et al.

(10) Patent No.: US 7,790,199 B2
(45) Date of Patent: *Sep. 7, 2010

(54) MODIFIED RELEASE DOSAGE FORMS OF SKELETAL MUSCLE RELAXANTS

(75) Inventors: Gopi Venkatesh, Vandalia, OH (US); James M. Clevenger, Vandalia, OH (US)

(73) Assignee: Eurand, Inc., Vandalia, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/236,723

(22) Filed: Sep. 24, 2008

(65) Prior Publication Data

US 2009/0017127 A1    Jan. 15, 2009

Related U.S. Application Data

(63) Continuation of application No. 10/713,929, filed on Nov. 14, 2003, now Pat. No. 7,387,793.

(51) Int. Cl.
A61K 9/14    (2006.01)

(52) U.S. Cl. ........................ 424/489; 424/401

(58) Field of Classification Search ............... None
See application file for complete search history.

(56) References Cited

U.S. PATENT DOCUMENTS

| | | | |
|---|---|---|---|
| 3,155,590 A | 11/1964 | Miller et al. | |
| 3,341,416 A | 9/1967 | Anderson et al. | |
| 3,488,418 A | 1/1970 | Holliday et al. | |
| 3,882,246 A | 5/1975 | Share | |
| 4,292,298 A | 9/1981 | Davis | |
| 4,590,062 A | 5/1986 | Jang | |
| 4,713,248 A | 12/1987 | Kjornaes et al. | |
| 4,728,513 A | 3/1988 | Ventouras | |
| 4,743,248 A | 5/1988 | Bartoo et al. | |
| 4,780,319 A | 10/1988 | Zentner et al. | |
| 4,780,463 A | 10/1988 | Sunshine et al. | |
| 4,789,549 A | 12/1988 | Khan et al. | |
| 4,795,644 A | 1/1989 | Zentner | |
| 4,814,183 A | 3/1989 | Zentner | |
| 4,839,177 A | 6/1989 | Colombo et al. | |
| 4,851,228 A | 7/1989 | Zentner et al. | |
| 4,851,229 A | 7/1989 | Magruder et al. | |
| 4,882,167 A | 11/1989 | Jang | |
| 4,919,938 A | 4/1990 | Lovegrove et al. | |
| 4,968,507 A | 11/1990 | Zentner et al. | |
| 4,996,047 A | 2/1991 | Kelleher et al. | |
| 5,008,114 A | 4/1991 | Loverecich | |
| 5,102,668 A | 4/1992 | Eichel et al. | |
| 5,120,548 A | 6/1992 | McClelland et al. | |
| 5,133,974 A | 7/1992 | Paradissis et al. | |
| 5,260,069 A | 11/1993 | Chen | |
| 5,275,824 A | 1/1994 | Carli et al. | |
| 5,350,584 A | 9/1994 | McClelland et al. | |
| 5,366,738 A | 11/1994 | Rork et al. | |
| 5,401,512 A | 3/1995 | Rhodes et al. | |
| 5,407,686 A | 4/1995 | Patel et al. | |
| 5,422,122 A | 6/1995 | Powell | |
| 5,582,838 A | 12/1996 | Rork et al. | |
| 5,607,671 A | 3/1997 | Heino | |
| 5,874,418 A | 2/1999 | Stella et al. | |
| 5,882,682 A | 3/1999 | Rork et al. | |
| 5,952,451 A | 9/1999 | Zhao | |
| 6,004,582 A | 12/1999 | Faour et al. | |
| 6,020,000 A | 2/2000 | Wong et al. | |
| 6,191,162 B1 | 2/2001 | Byrd | |
| 6,344,215 B1 | 2/2002 | Bettman et al. | |
| 6,358,944 B1 | 3/2002 | Lederman et al. | |
| 6,451,345 B1 | 9/2002 | Percel et al. | |
| 6,500,454 B1 | 12/2002 | Percel et al. | |
| 6,627,223 B2 | 9/2003 | Percel et al. | |
| 6,663,888 B2 | 12/2003 | Percel et al. | |
| 6,673,367 B1 | 1/2004 | Goldenheim et al. | |
| 7,387,793 B2 | 6/2008 | Venkatesh et al. | |
| 2003/0099711 A1 | 5/2003 | Meadows et al. | |
| 2003/0215496 A1 | 11/2003 | Patel et al. | |
| 2004/0126427 A1 | 7/2004 | Venkatesh et al. | |
| 2004/0166160 A1 | 8/2004 | Subramanian et al. | |
| 2004/0197407 A1 | 10/2004 | Subramanian et al. | |
| 2005/0013860 A1 | 1/2005 | Venkatesh et al. | |
| 2005/0106247 A1 | 5/2005 | Venkatesh et al. | |
| 2008/0124398 A1 | 5/2008 | Venkatesh et al. | |
| 2008/0124399 A1 | 5/2008 | Venkatesh et al. | |
| 2008/0279937 A2 | 11/2008 | Venkatesh et al. | |
| 2009/0017126 A1 | 1/2009 | Venkatesh et al. | |

FOREIGN PATENT DOCUMENTS

EP    0177000    4/1986

(Continued)

OTHER PUBLICATIONS

Akimoto, M. et al., "Evaluation of sustained-release granules of chlorphenesin carbamate in dogs and humans," International Journal of Pharmaceutics, 100, pp. 133-142 (1993).

(Continued)

*Primary Examiner*—Robert A Wax
*Assistant Examiner*—Bethany Barham
(74) *Attorney, Agent, or Firm*—Cooley LLP

(57) ABSTRACT

A unit dosage form, such as a capsule or the like, for delivering a skeletal muscle relaxant, such as cyclobenzaprine hydrochloride, into the body in an extended or sustained release fashion comprising one or more populations of drug-containing particles (beads, pellets, granules, etc.) is disclosed. At least one bead population exhibits a pre-designed sustained release profile. Such a drug delivery system is designed for once-daily oral administration to maintain an adequate plasma concentration—time profile, thereby providing relief of muscle spasm associated with painful musculoskeletal conditions over a 24 hour period.

14 Claims, 4 Drawing Sheets

FOREIGN PATENT DOCUMENTS

| EP | 0518263 A1 | 12/1992 |
|---|---|---|
| KR | 10-1999-0039518 | 4/2001 |
| WO | WO 81/02671 | 10/1981 |
| WO | WO 85/03437 | 8/1985 |
| WO | WO 98/06439 | 2/1998 |
| WO | WO 98/18610 | 5/1998 |
| WO | WO 98/53802 | 12/1998 |
| WO | WO 99/12524 | 3/1999 |
| WO | WO 99/18937 | 4/1999 |
| WO | WO 99/30671 | 6/1999 |
| WO | WO 01/15668 | 3/2001 |
| WO | WO 03/020242 | 3/2003 |

OTHER PUBLICATIONS

Complaint for Patent Infringement in *Eurand. Inc., Cephalon, Inc., and Anesta AG v. Impax Laboratories, Inc.*, Civil Action No. 1:09-cv-00018-SLR, filed with the United States District Court for the District of Delaware on Jan. 7, 2009.
Answer and Counterclaim of Impax Laboratories, Inc. in *Eurand, Inc., Cephalon, Inc., and Anesta AG v. Impax Laboratories, Inc.*, Civil Action No. 1:09-cv-00018-SLR, filed with the United States District Court for the District of Delaware on Jan. 26, 2009.
Eurand, Inc. and Anesta AG's Answers to Impax Laboratories, Inc.'s Counterclaims, *Eurand, Inc., Cephalon, Inc., and Anesta AG v. Impax Laboratories, Inc.*, Civil Action No. 1:09-cv-00018.SLR, filed with the United States District Court for the District of Delaware on Feb. 17, 2009.
Answer, Defenses, and Counterclaims of Mylan, Inc. and Mylan Pharmaceuticals, Inc., *Eurand, Inc., Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on Dec. 16, 2008.
Barr Laboratories, Inc.'s Answer, Affirmative Defenses and Counterclaims, *Eurand, Inc., Cephalon, Inc., and Anesta AG v. Mylan Pharmaceuticals, Inc., Mylan, Inc., Barr Pharmaceuticals, Inc. and Barr Laboratories, Inc.*, Civil Action No, 1:08-cv-00889-SLR, filed with the United States District Court for the District of Delaware on Dec. 16, 2008.
Eurand, Inc. And Anesta AG's Answers to Defendant Barr Laboratories, Inc.'s Counterclaims, *Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on Jan. 8, 2009.
Eurand, Inc., Cephalon. Inc., and Anesta AG's Answers and Affirmative Defenses to Mylan Inc. and Mylan Pharmaceuticals, Inc.'s Counterclaims, *Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on Jan. 30, 2009.
First Amended Answer, Defenses, and Counterclaims of Mylan, Inc. and Mylan Pharmaceuticals, Inc., *Eurand, Inc., Cephalon, Inc., and Anesta AG v. Mylan Pharmaceuticals. Inc., Mylan, Inc., Barr Pharmaceuticals, Inc. and Barr Laboratories, Inc.*, Civil Action No. 1:08-cv-00889-SLR, filed with the United States District Court for the District of Delaware on Apr. 30, 2009.
Eurand, Inc., Cephalon, Inc., and Anesta AG's Answers and Affirmative Defenses to Mylan Inc. and Mylan Pharmaceuticals, Inc.'s First Amended Counterclaims. *Eurand, Inc., Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on May 18, 2009.
Eurand, Inc., Cephalon. Inc., and Anesta AG's Notice of Voluntary Dismissal, *Eurand, Inc., Cephalon, Inc., and Anesta AG v. Mylan Pharmaceuticals, Inc., and Mylan, Inc.*, Civil Action No. 1:08-cv-00210-IMK, filed with the United States District Court for the Northern District of West Virginia on Feb. 23, 2009.
Detailed Factual and Legal Basis for Paragraph IV Certification Regarding United States Patent No. 7,387,793 (included in generic pharmaceutical company's Notice Letter dated May 28, 2009).
Remington: The Science and Practice of Pharmacy. 20$^{th}$ ed. (2000). pp. 898 and 995-1004.
Physician's Desk Reference, 57$^{th}$ ed. (2003), entry for Ritalin® LA (methylphenidate hydrochloride extended-release capsules).
Physician's Desk Reference, 57$^{th}$ ed. (2003), entry for Flexeril® (cyclobenzaprine hydrochloride).
International Search Report; PCT/US04/037266; Jun. 14, 2005.
Complaint for Patent Infringement in *Eurand, Inc., Cephalon, Inc., and Anesta AG v. Anchen Pharmaceuticals, Inc. and Anchen, Inc.*, Civil Action No. 1:09-cv-00492-SLR, filed with the United States District Court for the District of Delaware on Jul. 7, 2009.
Rowe et al., "Ethylcellulose," Handbook of Pharmaceutical Excipients, 5th ed., London: Pharmaceutical Press (2006), pp. 278-279.
Rekhi and Jambhekar, "Ethylcellulose—A Polymer Review," Drug Development and Industrial Pharmacy 21:61-77 (1995).
Excerpt from U.S. Pharmacopeia XXIV (1999), pp. xxvii-xxxvi (p. xxvii cited in Section I(A)(1) of C4).
Detailed Factual and Legal Basis for Paragraph IV Certification Regarding United States Patent No. 7,387,793 (included in generic pharmaceutical company's Notice Letter dated Oct. 28, 2008).
Complaint for Patent Infringement in *Eurand, Inc., Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on Nov. 25, 2008.
Complaint for Patent Infringement in *Eurand, Inc., Cephalon, Inc., and Anesta AG v. Mylan Pharmaceuticals, Inc. and Mylan, Inc.*, Civil Action No. 1:08-cv-00210-IMK, filed with the United States District Court for the Northern District of West Virginia on Nov. 26, 2008.
Copending U.S. Appl. No. 12/026,887 (divisional of U.S. App. No. 10/713,929), filed Feb. 6, 2008.
Notice of Allowance in Copending U.S. Appl. No. 12/026,887 (divisional of U.S. App. No. 10/713,929), filed Feb. 6, 2008.
Copending U.S. Appl. No. 12/026,882 (continuation of U.S. App. No. 10/713,929), filed Feb. 6, 2008.
Copending U.S. Appl. No. 12/236,719 (divisional of U.S. App. No. 10/713,929) filed Sep. 24, 2008.
Detailed Factual and Legal Basis for [Redacted] Paragraph IV Certification Regarding United States Patent No. 7,544,372 (included in generic pharmaceutical company's Notice Letter dated Feb. 19, 2010).
Dressman et al. (1995) "Circumvention of pH-dependent release from ethylcellulose-coated pellets" J. Controlled Release 36:251-260.
Lieberman ed. Pharmaceutical Dosage Forms, Tables vol. 3 (1990) 503-507.
Kimko et al. (1999) "Pharmacokinetics and Clinical Effectiveness of Methylphenidate" Clin. Pharmacokinet. 37(6):457-470.
Merck Index 12 ed. 1996 p. 2784.
Melanga, et al. (2009) "Cyclobenzaprine ER for muscle spasm associated with low back and neck pain: two randomized double-blind placebo-controlled studies of identical design" Current Medical Research and Opinions, 25(5):1179-1196.
Darwish, et al. (2008) "Single-dose pharmacokinetics of once-daily cyclobenzaprine extended release 30 mg versus 10 mg three times daily in healthy young adults" Clin. Drug Invest. 28(12):793-801.
http://www.fmcbiopolymer.com/LinkClick. aspx?fileticket=psXL0Mf_3Jw%3d&tabid=2945&mid=6182 accessed Feb. 25, 2010.
http://www.eurand.com/tech_custom_diffucaps.html accessed Feb. 25, 2010.
Carette et al., "Comparison of amitriptyline, cyclobenzaprine, and placebo in the treatment of fibromyalgia. A randomized, double-blind clinical trial," Arthritis. Rheum. 37(1):32-40 (1994).
Park, et al., "A New Formulation of Controlled Release Amitriptyline Pellets and its In Vivo/In Vitro Assessments," Arch. Pharm. Res. vol. 26, No. 7, pp. 569-574 (2003).

FDA, Guidance for Industry: "Extended Release Oral Dosage Forms: Development, Evaluation, and Application of In Vitro / In Vivo Correlations," (Sep. 1997).

Gupta et al., "Pharmacokinetic and Pharmacodynamic Characterization of OROS® and Immediate-Release Amitriptyline," J. Clin. Pharmacol. 48,71-78 (1999).

Ginsberg et al., "A Randomized Placebo-Controlled Trial of Sustained-Release Amitriptyline in Primary Fibromyalgia," J. Musculoskeletal Pain 4:37-47 (1996).

Jorgensen, "Comparative Bioavailability of a Sustained Release Preparation of Amitriptyline and Conventional Tablets," Eur. J. Clin. Pharmacol. 12: 187-190 (1977).

Liisberg et al., "A clinical trial comparing sustained release amitriptyline (Saroten® Retard) and conventional amitriptyline tablets (Saroten®) in endogenously depressed patients with simultaneous determination of serum levels of amitriptyline and nortriptyline," Acta Psych. Scand. 57:426-435 (1978).

Percel et al., "Development of Multi-Coated Formulations for Time-Controlled Pulsatile Drug Delivery of Water-Soluble Compounds," Eurand Poster (2002).

Razaghi and Schwartz, "Investigation of Cyclobenzaprine Hydorchloride Release from Oral Osmotic Delivery Systems Containing a Water-Swellable Polymer," Drug Devel. Indust. Pharm. 28(6):631-639 (2002).

Razaghi and Schwartz, "Release of Cyclobenzaprine Hydrochloride from Osmotically Rupturable Tablets," Drug Devel. Indust. Pharm. 28(6):695-701 (2002).

"Amitripyline," and "Cyclobenzaprine," pp. 85-86 and 472-473, The Merck Index: An Encyclopedia of Chemicals, Drugs, and Biologicals 13th ed. (2001).

U.S. Pharmacopeia XXIX, United States Pharmacopeial Convention, Inc., meeting at Washington D.C., Mar. 9-12, 1995.

Vyas et al., "Timed Pulsatile Circadian Rhythm Release (CRR) Dosage Forms for Histamine H2 Antagonist Nizatidine," presented at AAPS, Salt Lake City (2003).

Winchell et al., "Cyclobenzaprine Pharmacokinetics, Including the Effect of Age, Gender, and Hepatic Insufficiency," J. Clin. Pharma. 42:61-69 (2002).

"Amrix®," 2 pages, Cephalon, Inc. (2008).

Ellul, "Bioenhancement Technologies Improve Absorption of Insoluble Drugs in Normal Dosage Forms," The Int'l Pharm. Rev. (2007).

Brassuer, R., "Comparison en double entre l'Amitriptyline Diffucaps et l'Amitriptyline ordinaire duns les troubles du sommeil d'origine depressive," Acta Psychiat. Belg. 1975 vol. 75:182-189.

Lofland, et al., "Letters to the Editor," Clin. J. Pain 17(1):103-104 (2001).

"Amitripyline," and "Cyclobenzaprine," pp. 85-86 and 457, The Merck Index: An Encyclopedia of Chemicals, Drugs, and Biologicals 12th Ed. (1996).

Barr Laboratories, Inc.'s First Supplemental Response to Plaintiffs' Interrogatory No. 5 in *Eurand, Inc., Cephalon, Inc., and Anesta AG v. Mylan Pharmaceuticals, Inc., Mylan, Inc., and Barr Laboratories, Inc.*, Civil Action No. 08-889-SLR, filed with the United States District Court for the District of Delaware on Aug. 14, 2009.

Physician's Desk Reference, 57th ed. (1999), entry for Flexeril® (cyclobenzaprine hydrochloride).

"[Redacted] Detailed Statement of the Factual and Legal Bases for Its Opinion That U.S. Patent No. 7,544,372 Is Invalid, Unenforceable or Not Infringed by the Manufacture, Use or Sale of Its Cyclobenzaprine Hydrochloride, ER Capsules, 15 mg and 30 mg" (included in generic pharmaceutical company's Notice letter dated Sep. 18, 2009).

"Mylan's First Supplemental Responses to Plaintiffs' First Set of Interrogatories," 54 pages, in *Eurand, Inc., Cephalon, Inc., and Anesta AG v. Mylan Pharmaceuticals, Inc., Mylan, Inc,. and Barr Laboratories, Inc.*, Civil Action No. 08-889-SLR, filed with the United States District Court for the District of Delaware on Aug. 14, 2009.

"Impax's Supplemental Response and Objections to Plaintiffs' Interrogatory No. 5," 8 pages, in *Eurand, Inc., Cephalon, Inc., and Anesta AG v. Impax Laboratories, Inc.*, Civil Action No. 09-018 (SLR), filed with the United States District Court for the District of Delaware on Sep. 4, 2009.

"Detailed Factual and Legal Basis for [Redacted] ANDA Certification That U.S. Patent No. 7,544,372 B2 is Invalid, Unenforceable and/or Will Not Be Infringed" (included in generic pharmaceutical company's Notice letter dated Aug. 13, 2009).

Amidon, "Optimizing Oral Delivery: PK/PD and Controlled Release," presented at the Formulation Optimization and Clinical Pharmacology, A Capsugel Sponsored Conference at Tokyo, p. 16 (Apr. 23, 1999).

Second Amended Answer, Defenses, and Counterclaims of Mylan, Inc. and Mylan Pharmaceuticals, Inc., *Eurand, Inc., Cephalon, Inc., and Anesta AG v. Mylan Pharmaceuticals, Inc., Mylan, Inc., Barr Pharmaceuticals, Inc. and Barr Laboratories, Inc.*, Civil Action No. 1:08-cv-00889-SLR, filed with the United States District Court for the District of Delaware on Sep. 30, 2009.

U.S. Pharmacopeia XXIV, United States Pharmacopeial Convention, Inc., meeting at Washingtonn, D.C., Mar. 9-12, 1995, pp. 482, 959, 1942-1944.

Complaint for Declaratory Judgment in *Mylan Pharmaceuticals Inc. and Mylan Inc., v. Eurand, Inc., Cephalon, Inc. and Anesta AG*, Civil Action No. 1:10-cv-00306-SLR, filed with the United States District Court for the District of Delaware on Apr. 15, 2010.

Mona Darwish Deposition Transcript, *Eurand, Inc., Cephalon, Inc. and Anesta AG, v. Mylan Pharmaceuticals Inc., Mylan Inc.*, and *Barr Laboratories, Inc. v. Implax Laboratories, Inc.*, Apr. 22, 2010.

Plaintiffs Exhibit 1, cited in Mona Darwish Deposition Transcript.

Defendants Exhibit 1 (DDX 1), cited in Mona Darwish Deposition Transcript.

Defendants Exhibit 2 (DDX 2), cited in Mona Darwish Deposition Transcript.

Defendants Exhibit 3 (DDX 3), cited in Mona Darwish Deposition Transcript.

Defendants Exhibit 31 (DDX 31), cited in Mona Darwish Deposition Transcript.

Defendants Exhibit 33 (DDX 33), cited in Mona Darwish Deposition Transcript.

Defendants Exhibit 34 (DDX 34), cited in Mona Darwish Deposition Transcript.

Defendants Exhibit 35 (DDX 35), cited in Mona Darwish Deposition Transcript.

Defendants Exhibit 36 (DDX 36), cited in Mona Darwish Deposition Transcript.

Defendants Exhibit 37 (DDX 37), cited in Mona Darwish Deposition Transcript.

Defendants Exhibit 38 (DDX 38), cited in Mona Darwish Deposition Transcript.

Defendants Exhibit 39 (DDX 39), cited in Mona Darwish Deposition Transcript.

Defendants Exhibit 40 (DDX 40), cited in Mona Darwish Deposition Transcript.

Defendants Exhibit 41 (DDX 41), cited in Mona Darwish Deposition Transcript.

Defendants Exhibit 42 (DDX 42), cited in Mona Darwish Deposition Transcript.

Defendants Exhibit 43 (DDX 43), cited in Mona Darwish Deposition Transcript.

Defendants Exhibit 44 (DDX 44), cited in Mona Darwish Deposition Transcript.

Defendants Exhibit 45 (DDX 45), cited in Mona Darwish Deposition Transcript.

Defendants Exhibit 46 (DDX 46), cited in Mona Darwish Deposition Transcript.

Defendants Exhibit 47 (DDX 47), cited in Mona Darwish Deposition Transcript.

Mylan's Third Amended and Supplemental Responses to Plaintiff's First Set of Interrogatories in *Eurand, Inc., Cephalon, Inc., and Anesta, AG v. Mylan Pharmaceuticals, Inc., Mylan, Inc., and Barr Laboratories, Inc.*, Civil Action No. 08-889 (SLR), filed with the United States District Court for the District of Delaware on Mar. 11, 2010.

Barr Laboratories, Inc.'s Amended Second Supplemental Responses to Plaintiff's Interrogatory Nos. 2&5 in *Eurand, Inc., Cephalon, Inc., and Anesta, AG v. Mylan Pharmaceuticals, Inc., Mylan, Inc., and Barr Laboratories, Inc.*, Civil Action No. 08-889 (SLR), filed with the United States District Court for the District of Delaware on May 18, 2010.

Bogentoft, et al. (1978) "Influence of Food on the Absorption of Acetylsalicylic Acid from Enteric Coated Dosage Forms," Eur. J. Clin. Pharm., 14(5):351-355.

Drugs and the Pharmaceutical Sciences, *Multiparticulate Oral Drug Delivery* (vol. 65, 1994).

Aquacoat EDC Technical Brochure (1996).

2003 FDA Guidance for Industry on Bioavailability and Bioequivalence Studies.

2001 FDA Guidance for Industry on Statistical Approaches to Establishing Bioequivalence.

Chen, et al., (2001) "Bioavailability and Bioequivalence: An FDA Regulatory Overview," Pharmaceutical Research, I8(12):1645-1650.

Expert Report of Dr. Gordon Amidon, executed on Jun. 30, 2010, *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Feb. 17, 2009.

Expert Report of Paul J. Jarosz, executed on Jun. 28, 2010, *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Feb. 17, 2009.

Expert Report of James A. Forstner, executed on Jun. 30, 2010, *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Feb. 17, 2009.

Expert Report of Courtney V. Fletcher, Pharm. D. executed on Jun. 28, 2010, *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Feb. 17, 2009.

Rebuttal Expert Report of Peter G. Carroll, Ph.D. J.D. executed on Jul. 20, 2010 *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Jul. 21, 2010.

Rebuttal Expert Report of Daniel Weiner, Ph.D. executed on Jul. 22, 2010 *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Jul. 21, 2010. [Redacted].

Rebuttal Expert Report of Robert O. Williams, Ph.D. executed on Jul. 22, 2010 *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Jul. 21, 2010.

Rebuttal Expert Report of David Steiner, MD. executed on Jul. 22, 2010 *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Jul. 21, 2010.

Rebuttal Expert Report of Stanley Davis, Ph.D. executed on Jul. 21, 2010 *Cephalon,. Inc. and Anesta AG v. Mylan Pharmaceuticals, Inc., Mylan, Inc. and Barr Laboratories, Inc.*, Civil Action No. 1:09-cv-00018-SLR Filed with the United States District Court for the District of Delaware on Jul. 21, 2010. [Redacted].

Coated Pharmaceutical Dosage Forms, (eds. K H. Bauer, K Lehmann, H. P. Osterwald and G. Rothgang) 1988, medpharm GmbH Scientific Publishers, Stuttgart, Germany, Chapter 7) [Exhibit D, Rebuttal Expert Report of Robert O. Williams].

Aqueous Polymeric Coatings for Pharmaceutical Dosage Forms, Second Edition (ed. James W. McGinity) 1997, Marcel Dekker, Inc, New York, Chapter 8) [Exhibit E, Rebuttal Expert Report of Robert O. Williams].

Aqueous Polymeric Coatings for Pharmaceutical Dosage Forms, Second Edition (ed. James W. McGinity) 1997, Marcel Dekker, Inc, New York, Chapter 1) [Exhibit F, Rebuttal Expert Report of Robert O. Williams].

Aqueous Polymeric Coatings for Pharmaceutical Dosage Forms, Second Edition (ed. James W. McGinity) 1997, Marcel Dekker, Inc, New York, Chapter 3) [Exhibit G, Rebuttal Expert Report of Robert O. Williams].

Coated Pharmaceutical Dosage Forms, (eds. K H. Bauer, K Lehmann, H. P. Osterwald and G. Rothgang) 1988, medpharm GmbH Scientific Publishers, Stuttgart, Germany, Chapter 4) [Exhibit H, Rebuttal Expert Report of Robert O. Williams].

Breimer, *Future Challenges for Drug Delivery Research*, Adv. Drug. Delivery Revs. 33:265-68 (1998) [Exhibit A, Rebuttal Expert Report of Stanley Davis].

Gupta & Robinson, *Oral Controlled Release Delivery*, Chapter 6, Treatise on Controlled Drug Delivery (Kydonieus ed. 1987) [Exhibit B, Rebuttal Expert Report of Stanley Davis].

*Pharmacodynamic Aspects of Sustained Release Preparations*, Adv. Drug. Delivery 33:185-99, 195 (1988) [Exhibit C, Rebuttal Expert Report of Stanley Davis].

Skelly, et al., Workshop Report: In Vitro *and* in Vivo *Testing and Correlation for Oral Controlled/Modified-Release Dosage Forms*, Pharm. Res., 7(9): 975-982, 979 (1990). [Exhibit D, Rebuttal Expert Report of Stanley Davis].

Corrigan, *The Biopharmaceutic Drug Classification and Drugs Administered in Extended Release (ER) Formulations*, Adv. Exp. Med. Biol., (1997) [Exhibit E, Rebuttal Expert Report of Stanley Davis].

Wilding, et al., Gastrointestinal Transit and Systemic Absorption of Captopril From a Pulsed Release Formulation., Pharm. Res. 9(5):654-657 [Exhibit F, Rebuttal Expert Report of Stanley Davis].

Hoffman, et al., *Pharmacodynamic and Pharmacokinetic Rationales for the Development of an Oral Controlled-Release Amoxicillin Dosage Form*, J. Control Release, 54(1):29-37, (1998) [Exhibit G, Rebuttal Expert Report of Stanley Davis].

Qui & Zhang, *Research and Development Aspects of Oral Controlled-Release Dosage Forms*, Handbook of Pharmaceutical Technology, 23: 465-503, 473-75 (Wise ed. 2000) [Exhibit H, Rebuttal Expert Report of Stanley Davis].

Notari, Biopharmaceutics & Clinical Pharmacokinetics, at 208-10 (4th ed. 1987) [Exhibit I, Rebuttal Expert Report of Stanley Davis].

Chung, et al., Clinical Pharmacokinetics of Doxazosin in a Controlled-Relesae Gastrointestinal Therapeutic System (GITS) formulation, J. Clin. Pharmacol., 48:678-87 (1999) [Exhibit J, Rebuttal Expert Report of Stanley Davis].

Thombre, et al., *In Vitro/In Vivo Correlations of Sustained-Release Coated Multiparticulate Formulations of Doxazosin*, Int. J. Pharmaceutics, 111: 181-89 (1994) [Exhibit K, Rebuttal Expert Report of Stanley Davis].

Nielsen, et al., *Analgesic Efficacy of Immediate and Sustained Release Paracetamol and Plasma Concentration of Paracetamol. Double Blind Placebo-Controlled Evaluation Using Painful Laser Stimulation*, Eur. J. Clin. Pharmacol. 42:261-64, 263 (1992) [Exhibit L, Rebuttal Expert Report of Stanley Davis].

Castaneda-Hernandez, et al., *Differences in Nifedipine Concentration-Effect Relationship Between Capsule and Slow Release Tablet Administration*, Int'l J. of Clin. Pharmacol. & Therapeutics 33(1): 56-60, 59 (1995) [Exhibit M, Rebuttal Expert Report of Stanley Davis].

Skelly & Barr, *Regulatory Assessment*, Chapter 7, Controlled Drug Delivery, at 297-99 (Robinson & Lee ed. 1987) [Exhibit N, Rebuttal Expert Report of Stanley Davis].

Welling & Dobrinska, *Dosing Considerations and Bioavailability Assessment of Controlled Drug Delivery Systems*, Chapter 6, Controlled Drug Delivery, at 268-69 (Robinson & Lee ed. 1987) [Exhibit P, Rebuttal Expert Report of Stanley Davis].

Kramer & Blume, *Biopharmaceutical Aspects of Multiparticulates*, Chapter 12, Multiparticulate Oral Drug Delivery, at 310-11 (Sellassie ed. 1994) [Exhibit Q, Rebuttal Expert Report of Stanley Davis].

Mylan extended-release propranolol label [Exhibit R, Rebuttal Expert Report of Stanley Davis].

Serlin, et al., *The Pharmacodynamics and Pharmacokinetics of Conventional and Long-Acting Propranolol in Patients With Moderate Hypertension*, Br. J. Clin. Pharmac. 15:519-27 (1983) [Exhibit S, Rebuttal Expert Report of Stanley Davis].

Wikstrand, et al., *Pharmacokinetic Considerations of Formulation: Extended-Release Metoprolol Succinate in the Treatment of Heart Failure*, J. Cardiovascular Pharmacol., 41:151-57 (2003) [Exhibit T, Rebuttal Expert Report of Stanley Davis].

Sinemet Package Insert [Exhibit U, Rebuttal Expert Report of Stanley Davis].

Silver, et al., *Pharmacokinetics of Once-Daily Trospium Chloride 60 mg Extended Release and Twice-Daily Trospium Chloride 20 mg in Healthy Adults*, J. Clin. Pharmacol. 50:143-50 (2010) [Exhibit V, Rebuttal Expert Report of Stanley Davis].

DrugBank drug card for Cyclobenzaprine [Exhibit X, Rebuttal Expert Report of Stanley Davis].

Hucker, et al., *Plasma Levels and Bioavailability of Cyclobenzaprine in Human Subjects*, J. Clin. Pharmacol. 17(11-12):719-27, 726 (1977) [Exhibit Z, Rebuttal Expert Report of Stanley Davis].

Hucker & Stauffer, *GLC Determination of Cyclobenzaprine in Plasma & Urine*, J. Pharm. Sci. 65(8): 1253-55, 1254 (1976) [Exhibit AA, Rebuttal Expert Report of Stanley Davis].

DrugBank drug card for Pentoxifylline [Exhibit BB, Rebuttal Expert Report of Stanley Davis].

Takamatsu, et al., *Human Jejunal Permeability of Two Polar Drugs: Cimetidine and Ranitidine*, Pharm. Res., 18(6) 742-44 (2001) [Exhibit CC, Rebuttal Expert Report of Stanley Davis].

Basit, et al., *Influence of Polyethylene Glycol 400 on the Gastrointestinal Absorption of Ranitidine*, Pharm. Res., 19(9) 1368-74 (2002) [Exhibit DD, Rebuttal Expert Report of Stanley Davis].

DrugBank drug card for Methylphenidate [Exhibit EE, Rebuttal Expert Report of Stanley Davis].

DrugBank drug card for Amitriptyline [Exhibit FF, Rebuttal Expert Report of Stanley Davis].

Linden, *Cyclobenzaprine Overdosage*, J. Toxicol.-Clin. Toxicol., 20(3):281-88 (1983) [Exhibit GG, Rebuttal Expert Report of Stanley Davis].

Hawes, *N+-Glucuronidation, A Common Pathway in Human Metabolism of Drugs With a Tertiary Aminde Group, Drug Metab. & Disposition*, 26(9):830-37 [Exhibit II, Rebuttal Expert Report of Stanley Davis].

Doan, et al., *Passive Permeability and P-Glycoprotein-Mediated Efflux Differentiate Central Nervous System (CNS) and Non-CNS Marketed Drugs*, 303(3):1029-37 (2002) [Exhibit JJ, Rebuttal Expert Report of Stanley Davis].

Ray, et al., *Charcoal Bezoar, Small-Bowel Obstruction Secondary to Amitriptyline Overdose Therapy, Digestive Diseases and Sciences*, 33(1):106-07 (1988) [Exhibit KK, Rebuttal Expert Report of Stanley Davis].

Wilson, *Behaviour of Multiparticulate Systems Versus Monolithic Systems in the Gastrointesnital Tract*, Chapter 6, Multiparticulate Controlled Release Dosage Forms, at 94 (Melia, et al., ed. 1994) [Exhibit LL, Rebuttal Expert Report of Stanley Davis].

Dressman, et al., *Circumvention of pH-dependent Release from Ethylcellulose-Coated Pellets*, J. Controlled Release, 36:251-60 (1995) [Exhibit MM, Rebuttal Expert Report of Stanley Davis].

Luo X., et al., *Prescription of nonsteroidal anti-inflammatory drugs and muscle relaxants for back pain in the United States*, Spine, 2004; 29(23): E531—E537) [Exhibit OO, Rebuttal Expert Report of Stanley Davis].

Gupta et al., *Pharmokinetics of an Oral Once-a-Day Controlled Release Oxybutynin Formulation Compared with Immediate-release Oxybutynin*, J. Clin. Pharmacol. 39(289-296)(1999) [Exhibit RR, Rebuttal Expert Report of Stanley Davis].

MODIFIED RELEASE DOSAGE FORMS OF SKELETAL MUSCLE RELAXANTS

CROSS-REFERENCE TO RELATED APPLICATIONS

This application is a Continuation of U.S. application Ser. No. 10/713,929, filed Nov. 14, 2003, now U.S. Pat. No. 7,387,793, which is incorporated herein by reference in its entirety for all purposes.

TECHNICAL FIELD

A major objective of developing and commercializing controlled release dosage forms for indications such as cardiovascular diseases, chronic pain, relief of muscle spasm and associated symptoms especially in the elderly is to deliver the drug so as to maintain the drug at therapeutically effective concentrations over an extended period of time, thereby enhancing patient compliance and therapeutic efficacy, thereby reducing both cost of treatment and side effects.

BACKGROUND OF THE INVENTION

Many therapeutic agents are most effective when made available at a constant rate at or near the absorption site. The absorption of therapeutic agents thus made available generally results in desired plasma concentrations leading to maximum efficacy and minimum toxic side effects. Much effort has been devoted to developing matrix tablet based and multi-particulate capsule based drug delivery systems for oral applications.

U.S. Pat. No. 4,839,177 to Colombo, et al, assigned to Jagotec AG, refers broadly to controlled release of active substances including medicaments and any type of substance which is to be released at a controlled rate into an aqueous fluid. The patent is directed to a system for the controlled-rate release of active substances consisting of a deposit core comprising an active substance and at least one of (a) a polymeric material having a high degree of swelling on contact with water and a gellable polymeric material or (b) a single polymeric material having both swelling and gelling properties, and a support platform applied to the deposit core wherein the support platform consists of a water insoluble polymeric material.

U.S. Pat. No. 4,851,228 and U.S. Pat. No. 4,968,507, both to Zentner et al., assigned to Merck & Company, refer to a multi-particulate osmotic pump for the controlled release of a pharmaceutically active agent, each osmotic pump element consisting essentially of a core containing an active agent and a rate controlling water insoluble wall comprising a semi-permeable polymer and at least one pH insensitive pore forming additive dispersed throughout the wall. U.S. Pat. No. 4,590,062 to Jang assigned to Tech Trade Corporation and U.S. Pat. No. 4,882,167 to Jang, are directed to a compressed product containing an active produced by dry blending with a matrix combination of a hydrophobic polymer (e.g. ethylcellulose) and a wax, fatty acid, neutral lipid or combination thereof.

U.S. Pat. No. 4,996,047 to Kelleher, assigned to Richardson-Vicks, is directed to an oral pharmaceutical composition in unit dosage form of ion-exchange resin particles having a pharmacologically active drug bound thereto wherein the drug-resin complex particles have been coated with a water-impermeable diffusion barrier to provide controlled release of the active drug. U.S. Pat. No. 5,120,548 to McClelland et al., assigned to Merck & Company, is directed to a controlled release drug delivery device comprising a composition of a polymer which swells upon exposure to an aqueous environment, a plurality of controlled release swelling modulators, at least one active agent and either a water insoluble polymer coating surrounding the composition or a microporous wall surrounding the composition. U.S. Pat. No. 5,350,584 to McClelland et al., assigned to Merck & Company, relates to a process for the production of microcrystalline cellulose-free multiparticulates comprising a medicament and a charged resin. The resulting spheronized beads can be used in certain controlled release dosage forms.

U.S. Pat. No. 5,366,738 to Rork et al., assigned to Merck & Company, is directed to a drug delivery device for controlled release of an active agent. The drug delivery device includes a compressed core with an active agent and a polymer which forms gelatinous microscopic particles upon hydration and a water insoluble, water impermeable polymeric coating comprising a polymer and plasticizer which surrounds and adheres to the core.

U.S. Pat. No. 5,582,838 to Rork et al., assigned to Merck & Company, is related to a drug delivery device for the controlled release of a beneficial agent. The drug delivery device includes a compressed core having at least two layers: at least one layer is a mixture of a beneficial agent and a polymer which forms microscopic polymer gel beads upon hydration and at least one outer layer comprises a polymer which forms microscopic polymer gel beads upon hydration. A water insoluble, water impermeable coating is applied to the core and the coating has apertures exposing between about 5-75% of the core surface.

U.S. Pat. No. 5,874,418 to Stella et al., assigned to Cydex, is directed to a pharmaceutical composition comprising a carrier and a mixture of a sulfoalkyl ether-cyclodextrin and a therapeutic agent wherein a major portion of the therapeutic agent is not complexed to the sulfoalkyl ether-cyclodextrin derivative. Delayed, sustained or controlled release formulations are also described wherein the pharmaceutical core is coated with a film coating comprising a file forming agent and a pore forming agent. U.S. Pat. No. 5,882,682 to Rork et al., assigned to Merck & Company, is directed to a drug delivery process including the steps of preparing a uniform mixture of a polymer which forms gelatinous microscopic particles upon hydration, the beneficial agent and other excipients used in the preparation of the core; compressing the mixture into cores; coating the entire core with a water insoluble, water impermeable polymeric coating including a polymer and a plasticizer; and forming apertures through the coating.

U.S. Pat. No. 5,952,451 to Zhao, assigned to Guilford Pharmaceuticals is directed to a process for preparing high molecular weight poly(phosphoester) compositions comprising a biologically active substance and a poly(phosphoester) and the high molecular weight compositions produced thereby. The polymers so produced are useful in prolonged released drug delivery systems. U.S. Pat. No. 6,004,582 to Faour et al., assigned to Laboratorios Phoenix U.S.A., is directed to a multi-layered osmotic device comprising a compressed core including a first active agent and an osmotic agent, a semi-permeable membrane surrounding the core and having a preformed passageway therein wherein the membrane is permeable to a fluid in the environment of use and substantially impermeable to the first active agent. The semi-permeable membrane preferably consists essentially of cellulose acetate and poly(ethylene glycol). The external coat can includes poly(vinylpyrrolidone) and poly (ethylene glycol) and can further includes materials such as HPMC, ethylcellulose, hydroxyl ethylcellulose, CMC, dimethylaminoethyl methacrylate-methacrylic acid ester copolymer, ethyl acrylate-methyl methacrylate copolymer, and combinations thereof.

WO 99/18937 to Kleinbart et al., (Merck & Company), is directed to a composition comprising a pharmaceutically effective amount of cyclobenzaprine and calcium phosphate dibasic hydrous, wherein the tablet releases most of the active component within an hour. WO 99/30671 to Ron, is directed to an oral delivery vehicle including an aspected particle comprising a pharmaceutically active component and excipients wherein the vehicle is formulated to provide controlled delivery of the pharmaceutically active component. The vehicle may further contain a coating to provide sustained drug delivery to the particle. WO 98/53802 to Faour et al., (Laboratorios Phoenix USA), is directed to a multi-layered osmotic device that is capable of delivering a first active agent in an outer lamina to one environment of use and a second active agent in the core to another environment of use. An erodible polymer coat between an internal semipermeable membrane and a second active agent-containing external coat comprises poly(vinylpyrrolidone)-vinyl acetate) copolymer. The active agent in the core is delivered through a pore containing an erodible plug.

WO 98/18610 to Van Lengerich, is directed to particles containing an active agent, which provide controlled release of the active ingredient without substantial destruction of the matrix material. A release-rate controlling component is incorporated in a matrix to control the rate-release of the encapsulant from the particles. A hydrophobic component or a high water binding capacity component may be used for extending the release time. Release properties may also be controlled by precoating the encapsulant and/or coating the particles with a film-forming component. WO 98/06439 to Oedemoed, (Osteotech), is directed to a composition comprising a biologically active agent encapsulated in a matrix comprising a polyether ester copolymer, such as polyethylene glycol terephthalate/polybutylene-terephthalate copolymer. The polyether ester copolymer protects the active agent from degradation and thereby facilitates the drug delivery.

Cyclobenzaprine hydrochloride, a skeletal muscle relaxant, is a centrally acting drug which reduces or abolishes excessive tonic muscle activity in hypertonic as opposed to hyperphasic disorders. Flexeril IR (immediate release) tablets containing 10 mg of cyclobenzaprine HCl are administered three times a day to relieve skeletal muscle spasm of local origin without interfering with muscle function. The oral administration thrice daily is an issue of patient compliance, especially with the elderly. Hence, there is a need for modified release skeletal muscle relaxant suitable for a single administration. More particularly, there is a need for modified release (MR) cyclobenzaprine hydrochloride capsules, 15 and 30 mg, which would substantially minimize intersubject variability and improve the quality of life, especially in the elderly population.

SUMMARY OF THE INVENTION

The present invention provides a modified release, multi-particulate dosage form of a skeletal muscle relaxant comprising one or more bead populations which provides an extended release profile of the active under in vitro conditions closely mimicking the profile simulated from pharmaco-kinetic modeling. One of the bead populations is an ER (extended release) Bead population typically comprising a coating of a water insoluble polymer alone, or in combination with a water soluble polymer, applied onto active containing cores. The active core of the dosage form of the present invention may comprise an inert particle such as a sugar sphere, or an acidic or alkaline buffer crystal, which is coated with a skeletal muscle relaxant such as cyclobenzaprine hydrochloride-containing film-forming formulation, preferably a water-soluble film forming composition. The first coating formulation may contain, in addition to the active, a binder such as hydroxypropyl cellulose. The drug layered beads may be coated with a protective seal coating of OPADRY® Clear to produce IR Beads. Alternatively, the core particle may be formed by granulating and dry milling and/or by extrusion and spheronization of a pharmaceutical composition containing the active. The amount of drug in the core will depend on the dose required and typically varies from about 5 to about 60% by weight.

ER Beads can be produced by applying a functional membrane comprising a water insoluble polymer alone or in combination with a water soluble polymer onto IR Beads. The capsule formulation for once a day, oral administration of a skeletal muscle relaxant prepared in accordance with the present invention comprises ER Beads containing the active substance and optionally IR Beads. IR (immediate release) Beads allow immediate release of the active while ER Beads allow an extended release profile of the active over several hours. Upon oral administration, such a capsule formulation provides for therapeutically effective plasma profiles over an extended period of time, thereby resulting in improved patient compliance.

In accordance with one embodiment of the invention a pharmaceutical dosage form of a skeletal muscle relaxant is provided. The dosage form includes one or more bead populations and provides a modified release profile. At least one of the bead populations includes extended release (ER) beads wherein the ER beads include a core particle (IR (immediate release) bead) containing a skeletal muscle relaxant and an ER (extended release) coating comprising a water insoluble polymer surrounding the core. The dosage form, in accordance with certain embodiments, when dissolution tested using United States Pharmacopoeia Apparatus 2 (paddles @ 50 rpm) in 900 mL of 0.1N HCl (or a suitable dissolution medium) at 37° C. exhibits a drug release profile substantially corresponding to the following pattern:

after 2 hours, no more than about 40% of the total active is released;
after 4 hours, from about 40-65% of the total active is released;
after 8 hours, from about 60-85% of the total active is released; and
after 12 hours, from about 75-85% of the total active is released.

The dosage form thereby provides a therapeutically effective plasma concentration over an extended period of time, typically over a period of 24 hours to treat muscle spasm associated with painful musculoskeletal conditions in humans.

BRIEF DESCRIPTION OF THE DRAWINGS

The invention will be described in further detail with reference to the accompanying Figures wherein.

DETAILED DESCRIPTION OF THE INVENTION

Figure 1:
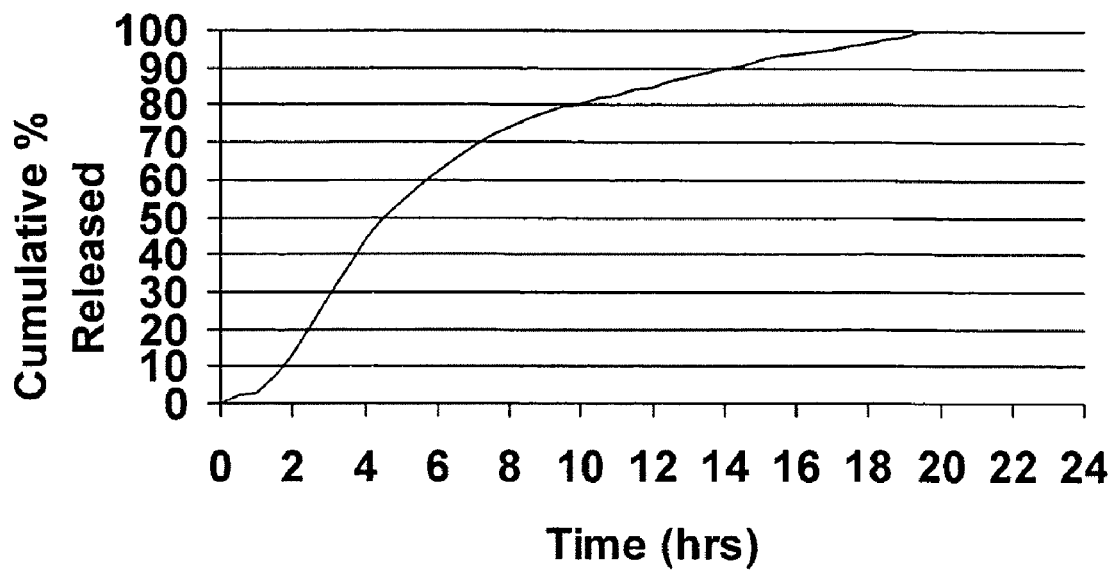
FIG. 1 shows the proposed target release profile for cyclobenzaprine hydrochloride MR (modified release) capsules, 15 and 30 mg.

All documents cited are, in relevant part, incorporated herein by reference; the citation of any document is not to be construed as an admission that it is prior art with respect to the present invention.

The active core of the dosage form of the present invention may be comprised of an inert particle or an acidic or alkaline buffer crystal, which is coated with a drug-containing film-forming formulation and preferably a water-soluble film forming composition to form a water-soluble/dispersible particle. Alternatively, the active may be prepared by granulating and milling and/or by extrusion and spheronization of a polymer composition containing the drug substance. The amount of drug in the core will depend on the dose that is required, and typically varies from about 5 to 60 weight %. Generally, the polymeric coating on the active core will be from about 4 to 20% based on the weight of the coated particle, depending on the type of release profile required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

The drug-containing particle may be coated with an extended release (ER) coating comprising a water insoluble polymer or a combination of a water insoluble polymer and a water soluble polymer to provide ER beads. In accordance with certain embodiments, the water insoluble polymer and the water soluble polymer may be present at a weight ratio of from 100/0 to 65/35, more particularly from about 95/5 to 70/30, and still more particularly at a ratio of from about 85/15 to 75/25. The extended release coating is applied in an amount necessary to provide the desired release profile. The extended release coating typically comprises from about 1% to 15%, more particularly from about 7% to 12%, by weight of the coated beads.

The present invention also provides a method of making a modified release dosage form including a mixture of two bead populations. In accordance with one embodiment, the method includes the steps of:

1. preparing a drug-containing core by coating an inert particle such as a non-pareil seed, an acidic buffer crystal or an alkaline buffer crystal with a drug and a polymeric binder or by granulation and milling or by extrusion/spheronization to form an immediate release (IR) bead;
2. coating the IR bead with a plasticized water-insoluble polymer alone such as ethylcellulose or in combination with a water soluble polymer such as hydroxypropylmethylcellulose to form an Extended Release (ER) bead;
3. filling into hard gelatin capsules ER Beads alone or in combination with IR Beads at a proper ratio to produce MR (modified release) capsules providing the desired release profile.

IR beads when tested in accordance with the following procedure release at least about 70%, more specifically at least about 90% of the active within 30 minutes.

Dissolution Procedure:

Dissolution Apparatus: USP Apparatus 2 (Paddles at 50 rpm), dissolution medium: 900 mL 0.1N HCl (or a suitable dissolution medium) at 37° C. and Drug Release determination by HPLC).

An aqueous or a pharmaceutically acceptable solvent medium may be used for preparing drug-containing core particles. The type of film forming binder that is used to bind the drug to the inert sugar sphere is not critical but usually water soluble, alcohol soluble or acetone/water soluble binders are used. Binders such as polyvinylpyrrolidone (PVP), polyethylene oxide, hydroxypropyl methylcellulose (HPMC), hydroxypropylcellulose (HPC), polysaccharides such as dextran, corn starch may be used at concentrations from about 0.5 to 5 weight %, although other concentrations may be useful. The drug substance may be present in this coating formulation in the solution form or may be dispersed at a solid content up to about 35 weight % depending on the viscosity of the coating formulation.

In accordance with certain embodiments, the drug substance, optionally a binder such as PVP, a dissolution rate controlling polymer (if used), and optionally other pharmaceutically acceptable excipients are blended together in a planetary mixer or a high shear granulator such as Fielder and granulated by adding/spraying a granulating fluid such as water or alcohol. The wet mass can be extruded and spheronized to produce spherical particles (beads) using an extruder/marumerizer. In these embodiments, the drug load could be as high as 90% by weight based on the total weight of the extruded/spheronized core.

Representative muscle relaxants include cyclobenzaprine, dantrolene sodium, methocarbamol, metaxalone, carisoprodol, diazepam and pharmaceutically acceptable salts or derivatives thereof. Cyclobenzaprine hydrochloride is a particularly useful muscle relaxant. As used herein, the useful muscle relaxants include the base, pharmaceutically acceptable salts thereof such as hydrochloride, stereoisomers thereof and mixtures thereof.

Representative examples of water insoluble polymers useful in the ER coating include ethylcellulose powder or an aqueous dispersion (such as AQUACOAT® ECD-30), cellulose acetate, polyvinyl acetate (Kollicoat SR#30D from BASF), neutral copolymers based on ethyl acrylate and methylmethacrylate, copolymers of acrylic and methacrylic acid esters with quaternary ammonium groups such as Eudragit NE, RS and RS30D, RL or RL30D and the like. Representative examples of water soluble polymers useful herein include low molecular weight hydroxypropyl methylcellulose (HPMC), methylcellulose, hydroxypropylcellulose, polyvinylpyrrolidone, polyethylene glycol (PEG of molecular weight>3000) and mixtures thereof. The extended release coating will typically be applied at a thickness ranging from about 1 weight % up to 15 weight % depending on the solubility of the active in water and the solvent or latex suspension based coating formulation used.

The coating compositions used in forming the membranes are usually plasticized. Representative examples of plasticizers that may be used to plasticize the membranes include triacetin, tributyl citrate, triethyl citrate, acetyl tri-n-butyl citrate diethyl phthalate, polyethylene glycol, polypropylene glycol, castor oil, dibutyl sebacate, acetylated monoglycerides and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying an extended release membrane coating or to separate the different membrane layers by applying a thin hydroxypropyl methylcellulose (HPMC) (OPADRY® Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention is applied to multi-dose forms, i.e., drug products in the form of multi-particulate dosage forms (pellets, beads, granules or mini-tablets) or in other forms suitable for oral administration. As used herein, these terms are used interchangeably to refer to multi-particulate dosage forms.

The invention also provides a method of making an extended release dosage form which includes a mixture of two or more bead populations. In accordance with one aspect of the present invention, the method includes the steps of:
  (a) coating an inert particle such as a non-pareil seed, an acidic buffer crystal or an alkaline buffer crystal with a drug and polymeric binder to form an active drug particle (IR beads), which may be present in the unit dosage form to act as a bolus dose;
  (b) coating the active drug particle with a solution or suspension of a water insoluble polymer or a mixture of water soluble and water insoluble polymers to form an extended release coated drug particle (ER beads);
  (c) filling into a hard gelatin capsule ER beads alone and optionally, in combination with IR beads at a proper ratio ranging from 95/5 to 70/30 (ER beads/IR beads) to produce a MR (modified release) capsule exhibiting a target drug release profile.

The following non-limiting examples illustrate the capsule dosage forms manufactured in accordance with the invention using cyclobenzaprine hydrochloride as a test case, which exhibit in vitro drug release profiles, similar to that predicted by performing modeling exercises. Such dosage forms when orally administered, would enable maintaining drug plasma concentrations at therapeutically effective levels over extended periods of time, thereby significantly improving patient compliance.

Example 1

Cyclobenzaprine is well absorbed after oral administration, but there is a large intersubject variation in plasma levels. It is eliminated quite slowly with a half-life as long as one to three days. The present treatment regimen of 10 mg three times daily is an issue of patient compliance, especially the elderly. Hence, a modified release dosage form (capsule) was designed with a release profile shown in FIG. 1. To determine if this is the proper release profile, the pharmacokinetics data of cyclobenzaprine following a single dose of 10 mg Flexeril® tablets administered 3 times a day was taken from the literature. A pharmacokinetic model was developed from this data using WinNonlin™ Version 1.5.

The resulting model parameters are listed below:

| Model Parameter | Value |
| --- | --- |
| Volume of Distribution/F | 429 L |
| K01 | 0.2031 $hr^{-1}$ |
| K10 | 0.1004 $hr^{-1}$ |
| K12 | 0.0828 $hr^{-1}$ |
| K21 | 0.0398 $hr^{-1}$ |
| Tlag | 0 hr |
| Dose | 2 × 10 mg Tablets |

Figure 2:
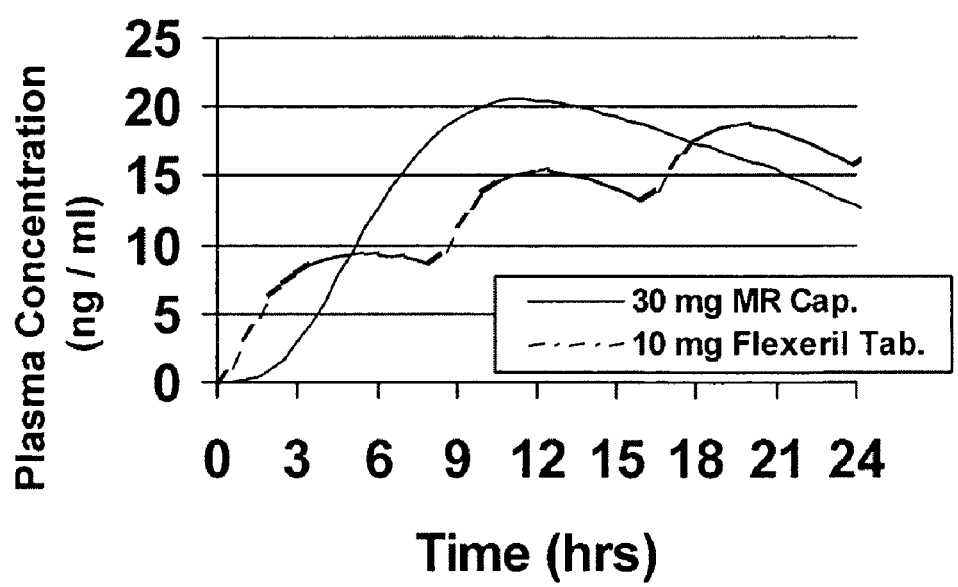
FIG. 2 shows the simulated Day 1 plasma level following dosing of 1×10 mg Flexeril® given. 3 times a day and 1×30 mg cyclobenzaprine HCl MR capsule given once-daily.

Theoretical plasma levels were simulated using the pharmacokinetic model given above and the target release rate given in FIG. 1. FIG. 2 shows the simulated plasma levels for day one following dosing of 1×10 mg Flexeril® Tablet given 3 times a day and the proposed Cyclobenzaprine HCl MR Capsule, 30 mg given once a day.

Example 2

Cyclobenzaprine Hydrochloride (1,200 g) was slowly added to an aqueous solution of polyvinylpyrrolidone such as Povidone USP (K-29/32, 80 g) and mixed well. #25-30 mesh sugar spheres (2,640 g) were coated with the drug solution in a Glatt fluid bed coater, equipped with a 9" bottom spray Wurster insert to provide IR beads with a coating weight of about 9%. The drug containing particles were dried, and a seal coat of OPADRY® Clear (2% w/w) was first applied and dried in the Glatt fluid bed unit as a precautionary measure to drive off excessive surface moisture. The composition and batch quantities of the IR Beads were given in 5 to 10 kg. Following the second coating process the IR Beads were passed through 14 and 25 mesh screens. Beads remaining on the 14-mesh screen were discarded as oversized beads and beads passing through the 25-mesh screen were discarded as undersized beads.

Figure 3:
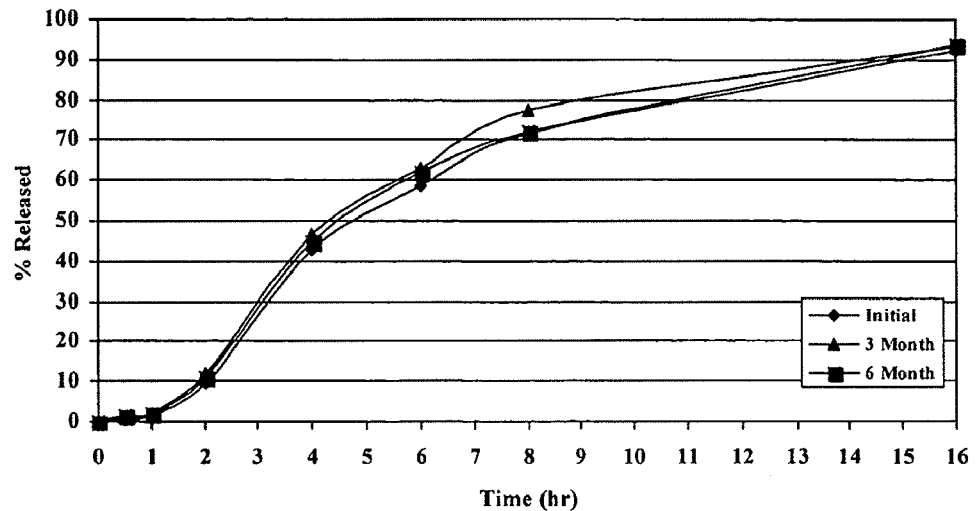
FIG. 3 shows the drug release profiles for cyclobenzaprine HCl ER (extended release) beads of Example 2.

The next step in the process was to apply an extended release polymer membrane by spraying AQUACOAT® ECD 30, an aqueous dispersion of ethylcellulose with dibutyl sebacate (76:24), onto the IR Beads for a weight gain of approximately 10%. The same fluid bed equipment was used to produce ER (extended release) Beads by further coating the AQUACOAT® coated beads with OPADRY® Clear for a weight gain of 2% w/w prior to curing at 60° C. in a conventional oven for a period of 24 hours. The batch size was 5 to 10 kg. The drug release profiles are shown in FIG. 3. The figure also shows the drug release profiles from ER Beads stored in induction sealed HDPE bottles at 25° C./60% RH for 6 months.

Example 3

Figure 4:
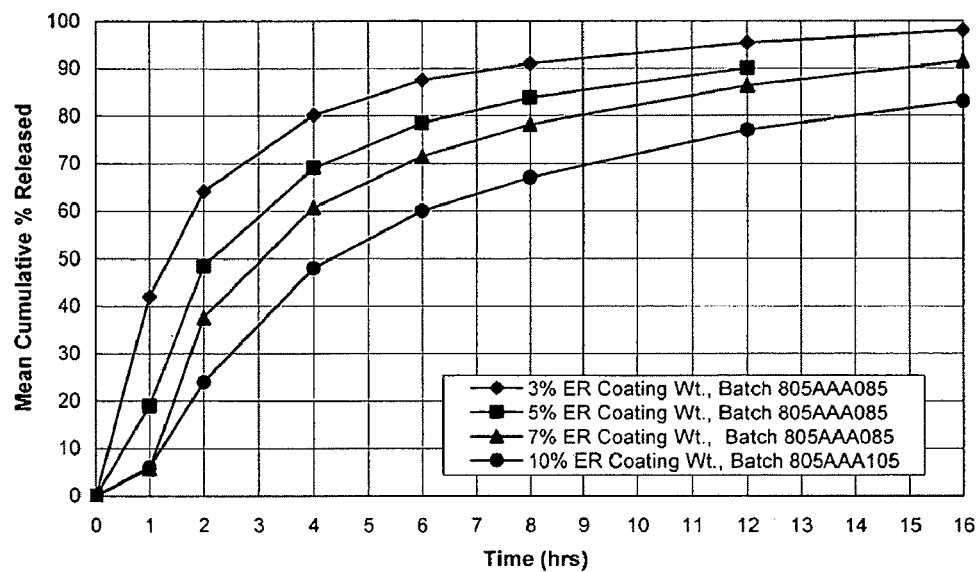
FIG. 4 compares the drug release profiles as a function of membrane coating of Example 3.

Cyclobenzaprine Hydrochloride (2.5 kg) was dissolved in 50/50 acetone/purified water. 25-30 mesh Sugar spheres, (7.3 kg) were coated with the drug solution in a Glatt fluid bed coater, equipped with a 9" bottom spray Wurster insert. The drug containing particles were dried, and a seal coat of OPADRY® Clear (2% w/w) was first applied and dried in the Glatt fluid bed unit as a precautionary measure to drive off excessive surface moisture. 910 g of ethylcellulose (Ethocel Premium Standard 10 cps) and 90 g of diethyl phthalate were dissolved in 98/02 acetone/purified water and applied onto the IR Beads (9 kg) in the Glatt GPCG 5 in accordance with the present invention. The release rates of the ER Beads will vary depending upon the film weight of the ER coating. One batch of IR Beads was coated for a final weight gain of 7% based on the weight of coated beads wherein samples of the ER Beads were removed during the ER coating process to yield beads with increasing coating weights. Another batch was coated for 10% weight gain and all the coated bead batches were cured at 60° C. for 4 hours in a conventional oven. FIG. 4 shows the relationship between the ER coating weights and the release rate of the finished ER coated Beads.

Figure 5:
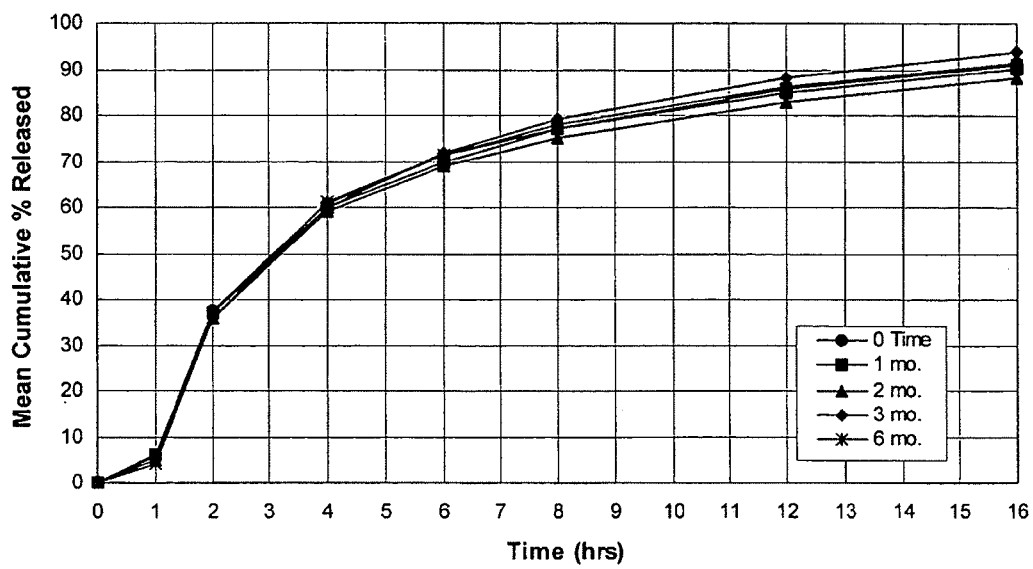
FIG. 5 shows the drug release profiles for cyclobenzaprine HCl ER beads of Example 3 stored in induction sealed HDPE bottles on accelerated stability.

A batch was coated with a 7% ER coating and cured at 60° C. for 4 hours. No changes were noted in the release rates, assay values or impurity levels after storage in HDPE bottles at 40° C./75% RH for a period of 6 months. The release rates for the samples are shown in FIG. 5.

Example 4

Figure 6:
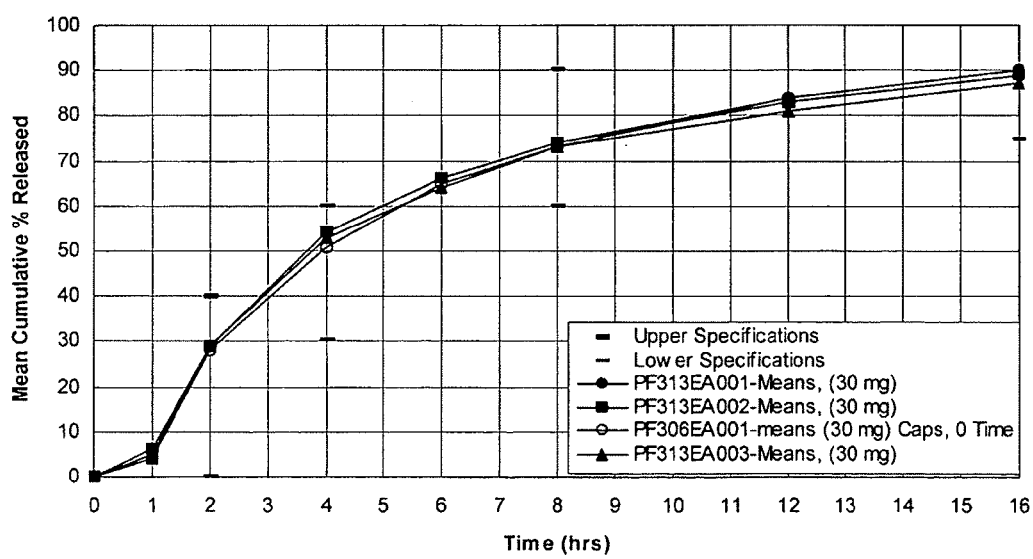
FIG. 6 shows the drug release profiles for 30 mg cyclobenzaprine HCl MR capsules of Example 4.

The drug layering, seal coating, and ER Coating processes were scaled-up to Glatt GPCG 120 equipped with an 18" bottom spray Wurster insert (batch size: 80 kg for IR Beads and 85 kg for ER Beads). The process parameters of each of the processes were optimized. The drug layering solution (9% weight gain), seal coating solution, and the ER coating solution (9% weight gain) were sprayed onto the sugar spheres or IR Beads while maintaining the product temperature between narrow limits. Following the seal or ER coating the beads were passed through 14 and 25 mesh screens discarding any beads remaining on the 14 mesh screen. The ER Beads were also cured at 60° C. for a period of 4 hours. The Extended Release Beads were then filled into size 4 capsules to produce Cyclobenzaprine HCl MR Capsules, 15 and 30 mg. The drug release profiles of 30 mg capsules of one pivotal clinical and three registration stability batches are presented in FIG. 6.

Example 5

Figure 7:
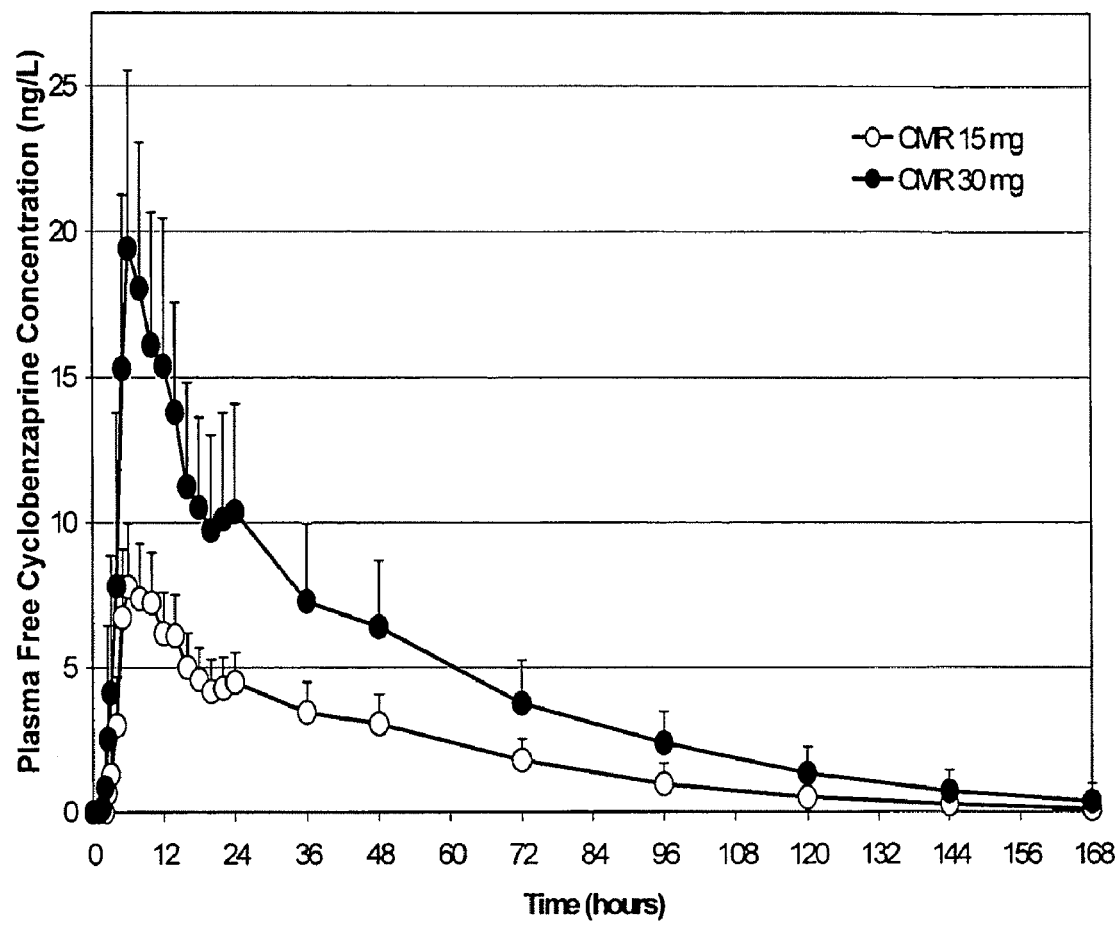
FIG. 7 shows the plasma levels for cyclobenzaprine HCl MR capsules, 15 and 30 mg of Example 5.

A Randomized double-blind two-period crossover study to assess the safety and bioavailability of Cyclobenzaprine HCl Modified-release (CMR) 15 mg and 30 mg in healthy male and female volunteers (N=14 or 15) was performed. Each subject received one 15 mg or 30 mg capsule of CMR in the morning, separated by a 14-day washout period between doses. The results are presented in Table 1 and FIG. 7 wherein $AUC_{0-168}$ refers to the area under the plasma concentration-time curve to the last measurable time point (168 hrs) calculated by the linear trapezoidal rule, $AUC_{0-\infty}$ refers to area under the concentration-time curve to infinity, $C_{max}$ refers to the maximum blood plasma concentration and $T_{max}$ refers to the time to maximum plasma levels of cyclobenzaprine.

TABLE 1

Pharmacokinetic Results: Mean (±SD) pharmacokinetic parameters are presented for subjects in the Safety population in the following table

|  | CMR 15 mg N = 15 | CMR 30 mg N = 14 |
| --- | --- | --- |
| $AUC_{0-168}$ (ng · hr/mL) | 318.30 ± 114.657 | 736.60 ± 259.414 |
| $AUC_{0-\infty}$ (ng · hr/mL) | 354.075 ± 119.8037 | 779.889 ± 277.6349 |
| $C_{max}$ (ng/mL) | 8.315 ± 2.1635 | 19.851 ± 5.8765 |
| Time to Peak, $T_{max}$ (hr) | 8.1 ± 2.94 | 7.1 ± 1.59 |
| Elimination Half-life, $t_{1/2}$ (hr) | 33.401 ± 10.2882 | 31.977 ± 10.1310 |

The treatments were significantly different from each other as values for AUCs and $C_{max}$ were higher for CMR 30 mg than those for CMR 15 mg. The bioavailability of CMR 30 mg was approximately twice that of CMR 15 mg as shown by the AUCs. The adjusted mean ratio of CMR 30 mg to CMR 15 mg was greater than about 2 for each of the AUCs and $C_{max}$, specifically the calculated values were 2.42 for $AUC_{0-168}$ (p<0.001), 2.286 for $AUC_{0-\infty}$ (p<0.001), and 2.424 for $C_{max}$ (p<0.001). Overall, both CMR 15 mg and 30 mg were well tolerated during the study.

Accordingly, one aspect of the invention relates to a dosage form containing cyclobenzaprine hydrochloride as a skeletal muscle relaxant wherein the pharmaceutical dosage form provides a maximum blood plasma concentration ($C_{max}$) within the range of about 80% to 125% of about 20 ng/mL of cyclobenzaprine HCl, an $AUC_{0-168}$ within the range of about 80% to 125% of about 740 ng·hr/mL and a $T_{max}$ within the range of about 80% to 125% of about 7 hours following oral administration of a single 30 mg cyclobenzaprine HCl MR Capsule.

While the invention has been described in detail and with reference to specific examples thereof, it will be apparent to one skilled in the art that various changes and modifications can be made without departing from the spirit and scope thereof.

What is claimed is:

1. A pharmaceutical dosage form comprising a population of extended release beads, wherein said extended release beads comprise:
   an active-containing core particle comprising cyclobenzaprine hydrochloride as the active; and
   an extended release coating comprising a water insoluble polymer membrane surrounding said core, wherein said water insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof;
   wherein the total amount of cyclobenzaprine hydrochloride in the pharmaceutical dosage form is 30 mg;
   wherein following a single oral administration of the pharmaceutical dosage form, the pharmaceutical dosage form provides a maximum blood plasma concentration ($C_{max}$) of 19.851±5.8765 ng/mL of cyclobenzaprine HCl and an $AUC_{0-168}$ of 736.60±259.414 ng·hr/mL.

2. A pharmaceutical dosage form comprising a population of extended release beads, wherein said extended release beads comprise:
   an active-containing core particle comprising cyclobenzaprine hydrochloride as the active; and
   an extended release coating comprising a water insoluble polymer membrane surrounding said core, wherein said water insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof;
   wherein the total amount of cyclobenzaprine hydrochloride in the pharmaceutical dosage form is 30 mg;
   wherein following a single oral administration of the pharmaceutical dosage form, the pharmaceutical dosage form provides a maximum blood plasma concentration ($C_{max}$) of 19.851±5.8765 ng/mL of cyclobenzaprine HCl and an $AUC_{0-\infty}$ of 779.889±277.6349 ng·hr/mL.

3. A pharmaceutical dosage form comprising a population of extended release beads, wherein said extended release beads comprise:
  an active-containing core particle comprising cyclobenzaprine hydrochloride as the active; and
  an extended release coating comprising a water insoluble polymer membrane surrounding said core, wherein said water insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof;
  wherein the total amount of cyclobenzaprine hydrochloride in the pharmaceutical dosage form is 15 mg;
  wherein following a single oral administration of the pharmaceutical dosage form, the pharmaceutical dosage form provides a maximum blood plasma concentration ($C_{max}$) of 8.315±2.1635 ng/mL of cyclobenzaprine HCl and an $AUC_{0\text{-}168}$ of 318.30±114.657 ng·hr/mL.

4. A pharmaceutical dosage form comprising a population of extended release beads, wherein said extended release beads comprise:
  an active-containing core particle comprising cyclobenzaprine hydrochloride as the active; and
  an extended release coating comprising a water insoluble polymer membrane surrounding said core, wherein said water insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof;
  wherein the total amount of cyclobenzaprine hydrochloride in the pharmaceutical dosage form is 15 mg;
  wherein following a single oral administration of the pharmaceutical dosage form, the pharmaceutical dosage form provides a maximum blood plasma concentration ($C_{max}$) of 8.315±2.1635 ng/mL of cyclobenzaprine HCl and an $AUC_{0\text{-}\infty}$ of 354.075±119.8037 ng·hr/mL.

5. A pharmaceutical dosage form comprising a population of extended release beads, wherein said extended release beads comprise:
  an active-containing core particle comprising cyclobenzaprine hydrochloride as the active; and
  an extended release coating comprising a water insoluble polymer membrane surrounding said core, wherein said water insoluble polymer membrane comprises a polymer selected from the group consisting of ethers of cellulose, esters of cellulose, cellulose acetate, ethyl cellulose, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, and mixtures thereof;
  wherein the total amount of cyclobenzaprine hydrochloride in the pharmaceutical dosage form is 30 mg;
  wherein following a single oral administration, said pharmaceutical dosage form provides a maximum blood plasma concentration ($C_{max}$) within the range of about 80% to 125% of about 20 ng/mL of cyclobenzaprine and an $AUC_{0\text{-}168}$ within the range of about 80% to 125% of about 740 ng·hr/mL.

6. The pharmaceutical dosage form of any one of claims 1-4, wherein said pharmaceutical dosage form when dissolution tested using United States Pharmacopoeia Apparatus 2 (paddled @ 50 rpm) in 900 mL of 0.1N HCl at 37° C. exhibits a release profile substantially corresponding to the following pattern:
  after 2 hours, no more than 40% of the total amount of the cyclobenzaprine hydrochloride is released;
  after 4 hours, from about 40-65% of the total amount of the cyclobenzaprine hydrochloride is released; and
  after 8 hours, from about 60-85% of the total amount of the cyclobenzaprine hydrochloride is released.

7. The pharmaceutical dosage form of any one of claims 1-5, wherein said pharmaceutical dosage form when dissolution tested using United States Pharmacopoeia Apparatus 2 (paddled @ 50 rpm) in 900 mL of 0.1N HCl at 37° C. exhibits a release profile substantially corresponding to the following pattern:
  after 2 hours, no more than 40% of the total amount of the cyclobenzaprine hydrochloride is released;
  after 4 hours, from about 40-65% of the total amount of the cyclobenzaprine hydrochloride is released;
  after 8 hours, from about 60-85% of the total amount of the cyclobenzaprine hydrochloride is released; and
  after 12 hours, from about 75-85% of the total amount of the cyclobenzaprine hydrochloride is released.

8. The pharmaceutical dosage form of any one of claims 1-5, wherein said extended release coating comprises from about 7% to 12% by weight of the extended release beads.

9. The pharmaceutical dosage form of any one of claims 1-5, wherein said extended release coating further comprises a water soluble polymer selected from the group consisting of methylcellulose, hydroxypropylcellulose, hydroxypropyl methylcellulose, polyethylene glycol, polyvinylpyrrolidone and mixtures thereof.

10. The pharmaceutical dosage form of any one of claims 1-5, wherein said extended release coating further comprises a plasticizer selected from the group consisting of triacetin, tributyl citrate, triethyl citrate, acetyl tri-n-butyl citrate, diethyl phthalate, dibutyl sebacate, polyethylene glycol, polypropylene glycol, castor oil, acetylated mono- and di-glycerides, and mixtures thereof.

11. The pharmaceutical dosage form of claim 10, wherein said extended release coating comprises about 10% to 25% by weight of said plasticizer.

12. The pharmaceutical dosage form of any one of claims 1-5, in the form of a capsule.

13. The pharmaceutical dosage form of any one of claims 1-5, wherein said extended release coating comprises about 1% to about 15% by weight of the extended release beads.

14. The pharmaceutical dosage form of any one of claims 1-5, wherein said pharmaceutical dosage form further comprises a seal coating layer comprising hydroxypropyl methylcellulose or hydroxypropylcellulose.

* * * * *